US 6,645,192 B2

(12) United States Patent
Kenison et al.

(10) Patent No.: US 6,645,192 B2
(45) Date of Patent: Nov. 11, 2003

(54) PELLET IMPLANT SYSTEM FOR IMMEDIATE AND DELAYED RELEASE OF ANTIPARASITIC DRUG

(75) Inventors: Dale C. Kenison, Overland Park, KS (US); Stanford R. Spurlin, Lenexa, KS (US)

(73) Assignee: Ivy Animal Health, Inc., Overland Park, KS (US)

( * ) Notice: Subject to any disclaimer, the term of this patent is extended or adjusted under 35 U.S.C. 154(b) by 0 days.

(21) Appl. No.: 09/163,646

(22) Filed: Sep. 30, 1998

(65) Prior Publication Data
US 2001/0049489 A1 Dec. 6, 2001

(51) Int. Cl.⁷ ............................................. A61M 31/00
(52) U.S. Cl. ........................ 604/506; 424/408; 424/423
(58) Field of Search ..................... 604/890.1, 891.1, 604/48, 502, 506, 59, 60–64, 93; 424/422–426, 438, 457, 408

(56) References Cited

U.S. PATENT DOCUMENTS

| 4,664,227 A | * | 5/1987 | Dietz et al. |
| 4,799,921 A | * | 1/1989 | Johnson et al. ............... 604/51 |
| 4,847,243 A | | 7/1989 | Wallace |
| 4,994,227 A | | 2/1991 | Dietz et al. |
| 5,035,891 A | | 7/1991 | Runkel et al. |
| 5,098,425 A | | 3/1992 | Eckenhoff |
| 5,200,196 A | | 4/1993 | Ayer et al. |
| 5,204,116 A | | 4/1993 | Edgren et al. |
| 5,340,588 A | * | 8/1994 | Domb ........................ 424/450 |
| 5,378,474 A | | 1/1995 | Morella et al. |
| 5,525,621 A | * | 6/1996 | Burt et al. ................... 514/393 |
| 5,609,884 A | | 3/1997 | Desai |
| 5,633,002 A | * | 5/1997 | Stricker et al. ............. 424/426 |
| 5,759,551 A | * | 6/1998 | Ladd et al. ............... 424/198.1 |
| 5,840,332 A | * | 11/1998 | Lerner et al. ............... 424/464 |
| 5,843,446 A | * | 12/1998 | Ladd et al. ............... 424/184.1 |
| 5,874,098 A | * | 2/1999 | Stevens et al. ............. 424/408 |
| 5,891,845 A | * | 4/1999 | Myers ........................ 514/11 |

FOREIGN PATENT DOCUMENTS

| WO | WO96/25852 | 8/1996 |
| WO | 99/15166 | 4/1999 |
| WO | WO99/51201 | 10/1999 |

* cited by examiner

Primary Examiner—Brian L. Casler
Assistant Examiner—Kevin C. Sirmons
(74) Attorney, Agent, or Firm—Sonnenschein Nath & Rosenthal; G. Harley Blosser; Lara Dickey Lewis

(57) ABSTRACT

A parasiticidal pellet system which delivers both immediate and long term control of parasite infestation in an animal as part of a single implant procedure. The system includes an implanter apparatus for subcutaneously implanting parasiticidal pellets in an animal through the bore of a hypodermic needle which is operably coupled to a pellet magazine, and a plurality of pellets sized to be implanted through the needle and positioned in the magazine for selective alignment of a pellet with the needle. The pellets include at least one immediate release parasiticidal agent first dose pellet and at least one extended release parasiticidal agent dose second pellet. The combined pellets are packaged in the magazine in sequential order for simultaneous delivery of an immediate dose and an extended dose as part of a single injection.

8 Claims, 1 Drawing Sheet

PELLET IMPLANT SYSTEM FOR IMMEDIATE AND DELAYED RELEASE OF ANTIPARASITIC DRUG

BACKGROUND OF THE INVENTION

The present invention is broadly concerned with a pellet implant system that simultaneously administers both an immediate parasiticidal dosage first component and a long term release parasiticidal dosage of a second component placed in subcutaneous pellets in order to control internal and external parasites in domesticated and wild animals. More particularly, it is concerned with an implanter having a pellet magazine containing parasiticidal pellets with an associated injection needle, as well as structure permitting injection of the pellets from the magazine through the needle for implantation under the skin of a animal. The pellets are formulated to deliver two separate doses simultaneously. The first dose is a parasiticidal dose which is immediately available for absorption. The second dose is a parasiticidal dose which is available for sustained absorption through bioerosion and diffusion over an extended period of time.

The importance of parasite control in animals used for meat and other agriculture production, recreation and companionship is well recognized. Meat, milk and fiber producing animals, such as suckling, growing, grazing and feed lot cattle, domesticated swine, sheep, goats, poultry and companion animals such as horses, dogs and cats all serve as hosts for a large number of internal and external parasites. The presence of such parasites is known to reduce overall production in animals producing meat and other agricultural products. In the case of companion and recreational animals, the presence of parasites can lead to discomfort, impaired health and performance, and even death.

Wild animal populations infested with parasites may experience substantial harmful effects as well as reduced reproductive efficiency. Such harmful effects are of particular concern in populations of endangered species, since it may impair attempts to reintroduce the species into an environment or to build the species population up to a level which can be easily sustained by natural growth. Endangered mammalian species which are maintained or managed in limited area preserves such as game preserves, animal parks, national parks or wildlife areas as well as zoo animals which are maintained in confined areas, are particularly susceptible to parasite infestation since they inhabit areas substantially smaller than their natural habitats, with denser populations of both parasites and their animal hosts.

Implant technology, that is to say, subcutaneous implant of pharmaceuticals and medical devices, is now well accepted and widespread in the fields of animal health and production enhancement and human health. Many types of biologically active compounds, including hormones, vitamins, antibiotics, antiinflammatory agents, vaccines and biocides are administered as solid compressed pellets which are injected by an implanter equipped with a hypodermic needle. The needle is used to make a small self-sealing and noncoring implant-receiving puncture beneath the skin at a suitable location on the body of the animal. Small pellets of the bioactive compound are forced through the needle and left under the skin as the needle is removed. The ears are a preferred site for pellet implantation in livestock such as cows, pigs and sheep. Implanted ears are commonly discarded in slaughtering, so that no unabsorbed pellet residue will end up in food products intended for consumption by humans or domestic animals.

The pellets are normally implanted in farm animals while the animal is confined in a chute. An ear is grasped in one hand, and an implanter device having a large hypodermic needle is used to puncture the hide and subcutaneously inject a pellet dose into an implant-receiving puncture. Implantation must be done carefully to ensure that the pellets are properly placed and that no portion of the pellet remains extending from the puncture outside the hide. The procedure must also be carried out quickly since the animals are not entirely cooperative and may shake their heads to free the held ear.

U.S. Pat. No. 5,522,797 (hereinafter "the '797 patent"), and entitled Slide Action Veterinary Implanter, which patent is hereby incorporated by reference, discloses an implanter which employs a slide action mechanism to retract an impeller, store an impeller driving force in a spring in cooperation with a latch mechanism, reset a trigger, and advance a pellet magazine, all by a single trigger actuated reciprocation of the slide mechanism. Operation of the trigger also forces the pellets from the magazine through the needle and under the skin of the animal.

Efficient implanters such as that taught in the '797 patent permit rapid sequential injection of many animals in a single session and make implant technology particularly well-suited for administration of parasiticides while the animals are confined for ear tagging, branding, veterinary procedures or the like. Even where only a single animal is to be treated, implantation offers a particularly safe method for administering certain biocides, so as to allow a user to avoid biocides that could be toxic if ingested by the animal, for example by licking off residue left on its own hide or fur or on that of another animal following treatment by dipping, spraying or dusting.

A number of effective compounds are available for internal and external parasite control, including the polyketide avermectins, the milbemycins and milbemycin oximes, fenbendazole and lufeneron. The most commonly used avermectins are ivermectin, doramectin, moxidectin, eprinomectrin and abamectin. However, such parasiticidal compounds have not previously been available in implantable pellet formulations which provide for immediate as well as extended release of the parasiticide.

Previous avermectin and milbemycin implants such as disclosed by Hepler in PCT application WO 9625852 and by Wallace in U.S. Pat. No. 4,847,243 do not provide prolonged controlled release of the parasiticide dose. Consequently, additional parasiticidal pellets must be periodically implanted in host animals to treat parasites in the immediate environment of the host animal.

This requirement for periodic readministration is not only cumbersome and inefficient, it increases the likelihood that a dose will be delayed or missed altogether and that parasites endemic to the environment will reinfest the host animal. Moreover, each such procedure subjects the animal to stress and risk of infection at the injection site.

A variety of techniques are currently employed to obtain sustained release of parasiticides. Oral boluses are formulated in double walled cylinders, with layers of racemates of active ingredients, with outer and inner layers having polymer coatings, with wax and fat to retard dissolution, and with a heat responsive carriers.

While such measures provide for sustained release of parasiticides over many hours, they do not obviate the need for periodic redosing. Effective parasite control requires prolonged sustained release for periods of up to several months in order to interrupt the parasite life cycle in the environment of the host animal.

Accordingly, there is a need for a system which delivers subcutaneously pellet implants of varying controlled release parasiticidal dosages to provide immediate as well as sustained release of the parasiticide for a period of up to several months, and which does so without requiring periodic redosing.

SUMMARY OF THE INVENTION

The present invention resolves the problems previously outlined and provides a greatly improved parasiticidal pellet system which delivers separate doses of both immediate and long term control of parasite infestation in an animal as part of a single implant procedure wherein the immediate dose is sufficient to kill pests already present in the animal and the long term dose is sufficient to prevent reinfestation.

Broadly speaking, the pellet system includes an implanter apparatus for subcutaneously implanting parasiticidal pellets in an animal through the bore of a hypodermic needle which is operably coupled to a pellet magazine, and a plurality of pellets sized to be implanted through the needle and positioned in the magazine for selective alignment of a pellet with the needle. The pellets include at least one immediate release parasiticidal agent first dose pellet and at least one extended release parasiticidal agent dose second pellet. The combined pellets are packaged in the magazine in an individual dosing chamber for simultaneous delivery of an immediate dose and an extended dose as part of a single injection. Advantageously, the system permits both immediate and sustained release of an effective dose of the parasiticidal agent, in order to control present parasite infestation and release sufficient agent over time to prevent reinfestation for a period of up to about 150 days. The immediate and sustained release agents may be the same or different parasiticidal agents with the principal difference between the agents being that the immediate agent is formulated to completely release into the system of the animal very quickly after implanting to provide a sufficient systemic amount of the immediate agent to kill pests that are currently in the animal and the sustained agent is formulated in a slow release matrix that slowly releases the sustained agent over a comparatively long time, for example about 150 days, in a sufficient amount to systemically prevent reinfestation of the animal.

OBJECTS AND ADVANTAGES OF THE INVENTION

The principal objects and advantages of the present invention include: providing a multicomponent parasiticidal pellet system; providing a pellet system for immediate as well as sustained delivery of a parasiticide in order to kill both internal and external parasites present on an animal and which may reinfest the animal in the future; providing a pellet system which includes an implanter apparatus for subcutaneously injecting pellets in an animal through the bore of a hypodermic needle which is operably coupled to a pellet magazine and simultaneously introduces separate immediate and extended release parasiticidal pellet doses; providing such a system and method which permits injection of predetermined doses of each of a parasiticide for immediate release and a parasiticide for extended release in a single injection; providing such a system and method which permits subcutaneous injection of both an immediate release parasiticidal dose and an extended release parasiticidal dose; providing such a system and method which permits an operator to selectively inject an extended release parasiticidal dose into the needle; providing such a system and method which permits serial injection of large numbers of animals in a single session; providing such a system and method which may employ a wide range of parasiticidal agents for use in control of infestation; providing such a system and method which is simple and efficient and economical to manufacture, which effectively prevents reinfestation of the animal for a period of up to about 150 days and which is particularly well-adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

Figure 1:
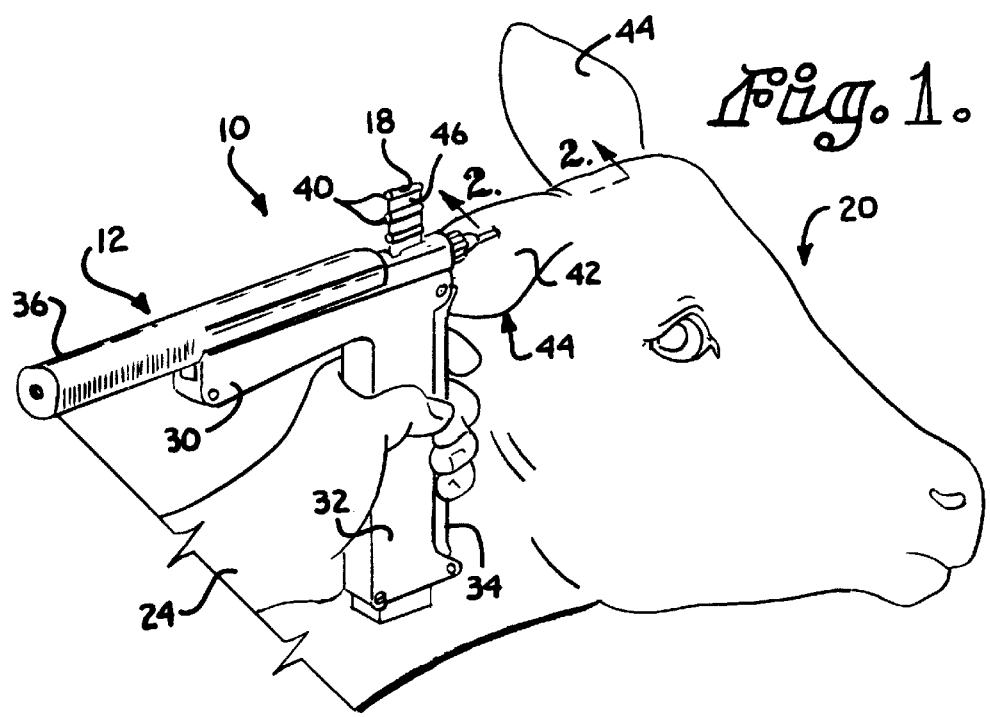
FIG. 1 is a fragmentary perspective view of a cow, an implanter apparatus in accordance with the present invention, and an apparatus operator.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring now to the drawing, the reference numeral 10 represents a pellet implantation system in accordance with the invention. The implantation system 10 broadly includes a slide action implanter apparatus 12 which is used to implant solid form bioactive compounds in various formulations, such as immediate release compressed pellets 14 and extended release compressed pellets 16 (FIG. 2) from a magazine strip 18 into an animal 20 through a hypodermic needle 22. The needle 22 is utilized by an operator 24 to create an opening 26 that produces an implant receiving puncture 28 in the animal 20.

A suitable implanter apparatus 12 is illustrated and described in detail in the '797 patent, and generally includes a housing 30 having a finger grip 32 with a trigger assembly 34 pivotally mounted therein. An impeller 36 is slidably mounted within the housing 30 in alignment with an interior bore 38 of the needle 22 and aligned chambers 40 of the loaded pellet magazine strip 18. The needle 22 is used to puncture through skin or hide 42 of an animal's ear 44 at the opening 26, and the trigger 34 is squeezed toward the grip 32 of the housing 30 to initiate injection of the pellets 14 and 16 and so as to cause the impeller 36 to be urged through the magazine chamber 40 and needle bore 38, thereby forcing the pellets 14 and 16 through the bore 38 of needle 22 and into the puncture 28 in the ear 44.

Each magazine strip 18 of the implanter 12 typically contains multiple parallel aligned pellet doses stored in corresponding pellet chambers 40, which are connected by interconnecting webs 46. The chambers 40 are slightly conical in shape and are arranged in a side-by-side parallel relation. The chambers 40 may have internal frictional formations such as beads or posts (not shown) to retain the pellets 14 and 16 therein prior to insertion and which can be easily bypassed by application of pressure to the trigger 34. A plurality of strips 18 can be connected in end-to-end relation to increase the implanting capacity before the implanter 12 requires reloading. When the pellets 14 and 16 in an individual magazine strip 18 are exhausted, the empty strip 18 can be detached from the remaining strips 18 located in the implanter 12 and discarded.

In the present embodiment, each pellet chamber 40 is loaded with a single immediate release parasiticidal agent dose pellet 14 and five extended release parasiticidal agent dose pellets 16. The pellets 14 and 16 are composed of an effective amount of one or more parasiticidal agents, formed into a compressed pellet in conjunction with one or more excipients.

A wide range of active ingredients may be employed as parasiticidal agents, for example, the polyketide avermectins, such as ivermectin, doramectin, moxidectin, eprinomectrin and abamectin, the milbemycins and milbemycin oximes, fenbendazole and lufeneron. As used herein the term parasiticide is intended to include parasiticides as noted above and other compositions that operably function under the present invention like parasiticides in combating and preventing reinfestation by internal and external parasites and which may be used internally in the particular species of animal to be treated by the invention. It is noted that the amount of parasiticidal agent required to produce the desired treatment varies with respect to the species and size of the animal to be treated. For example, when treating cattle the immediate release pellet preferably contains between about 25 and 125 milligrams of ivermectin and the sustained released combined pellets contain between about 50 and 175 milligrams of ivermectin. Parasiticidal agents having extended circulatory half-lives, such as ivermectin, are particularly preferred.

The pellets are uniquely and separately formulated so as to be biodegradable in the target animal and to control release of the parasiticide at different rates. The extended release pellets 16 are formulated to combine an effective dose of a parasiticidal agent such as ivermectin, with binding agent excipients that lengthen the implant delivery period by extending pellet 16 integrity and limiting pellet hydration by extracellular fluid entry into the pellet 16. In this manner, the extended pharmacokinetics of the parasiticidal agent, delayed bioerosion of the pellet, and delayed diffusion of the agent dose cooperatively result in an extended release pellet which makes available for absorption an effective dose of parasiticidal compound over a period of up to 150 days.

Any of a number of excipients may be employed in the extended release pellets 16, including lactose, polyethylene glycol, as sold under the trademark Carbowax®, by Union Carbide, magnesium stearate, cellulose and its derivatives, especially ethylcellulose as sold under the trademark Ethocel® by Dow, polymeric supports, binders and coloring agents.

The immediate release pellets 14 make the parasiticide available for absorption into the bloodstream of the animal immediately and may include the previously listed excipients as well as disintegration aids such as magnesium stearate and croscarmellose sodium, especially as sold under the trademark Ac-Di-Sol® by FMC and microcrystalline cellulose, especially as sold under the trademark Avicell® by FMC.

Each intermediate release pellet 14 is formulated to dissolve and enter the animal's blood system (systemically) within a few days, preferably within hours of injection. The extended release pellets 16 are formulated to release active parasiticide into the animal's blood system slowly and continuously over a period of many days, for example about 150 days, in order to sustain sufficient parasiticide systemically in the animal being treated to prevent reinfestation by undesirable pests.

The compressed pellets 14, 16 can be produced inexpensively and in large quantities by a variety of conventional manufacturing equipment.

In the illustrated embodiment, one pellet 14 incorporates an immediate release parasiticidal dose and the other five pellets 16 incorporate an extended release parasiticidal dose. It is foreseen that the number of pellets within an individual dosing chamber 40 within a magazine 18 for each release formulation within may vary, depending on the desired dose of parasiticide to be delivered. As an example, the extended release pellets 16 may number one or many, such as the illustrated five.

Each magazine chamber 40 is prefilled with a preferred number of discrete pellets 14 and 16, each containing a parasiticidal dose in a compressed pellet formulation designed respectively for immediate and extended release, the chamber 40 containing at least one immediate release pellet 14 and one extended release pellet 16. The magazine strip 18 is preferably loaded onto implanter housing 30 in an orientation so that the immediate release parasiticidal pellet 14 will be delivered first, followed by the extended release parasiticidal pellets 16.

Figure 2:
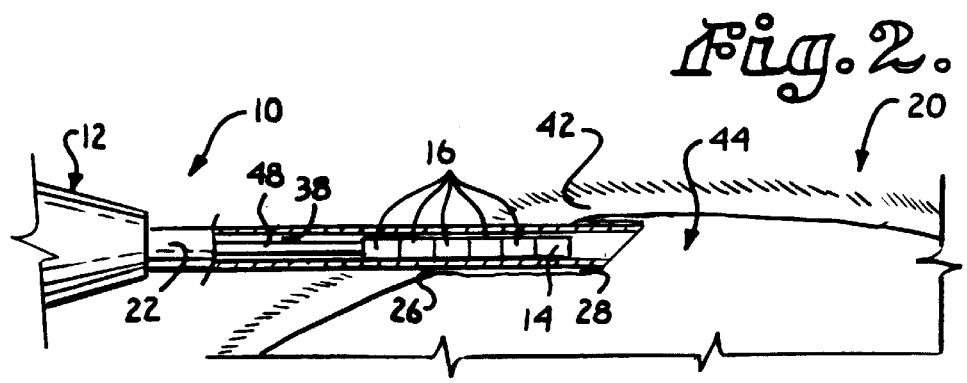
FIG. 2 is an enlarged, fragmentary cross-sectional view, taken along line 2–2 of FIG. 1, illustrating a hypodermic needle with pellets inside the needle being inserted into an ear of the cow.
Figure 3:
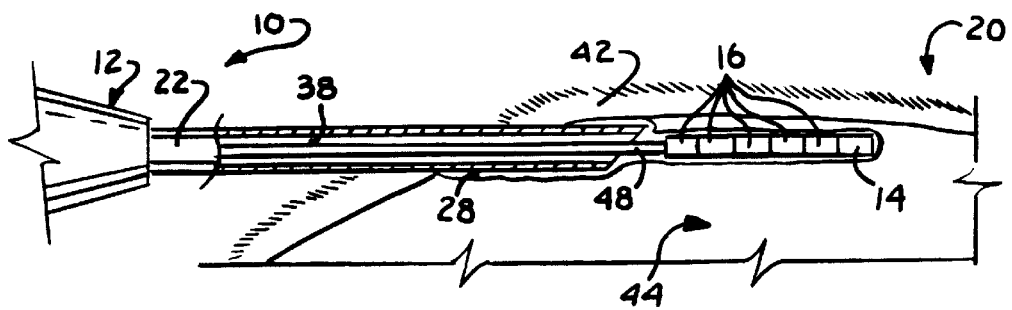
FIG. 3 is an enlarged, fragmentary cross sectional view similar to FIG. 2, illustrating subcutaneous placement of a stack of pellets by the implanter into the ear of the cow.

In use, an operator grasps the implanter 12 by the grip 32 and urges the needle 22 into the hide 42 and under the skin of the target animal 20 to make the implant receiving puncture 28. The puncture 28 shown in FIG. 2, is approximately half complete and is complete in FIG. 2. The operator 24 depresses the trigger member 34, thereby propelling a pin 48 of the impeller member 36 forwardly through an aligned magazine chamber 40, forcing the pellets 14 and 16 through the needle bore 38 and into the implant receiving puncture 28. The operator 24 then withdraws the needle 22, leaving the pellets 14 and 16 in the implant receiving puncture 28.

The bioerodible excipient disintegration aids included in the formulation of immediate release pellet 14 allows the pellet 14 to immediately make available for systemic absorption an effective dose of a parasiticidal compound, such as ivermectin. The long circulatory half-lives of such compounds ensures protection of the animal against parasites for up to 30 days. The binders included in the extended release pellets 16 cause delayed bioerosion of the pellets and diffusion of the effective dose of the parasiticidal compound for absorption into the bloodstream of the animal over an additional period of up to 120 days. This multicomponent formulation lengthens the pellet delivery period for the parasiticidal compound dose so that effective blood levels of the parasiticidal compound are maintained for periods of up to 150 days. In this manner, the internal and external parasites of the host animal are eliminated, and the animal is protected from reinfestation until the parasite life cycle in the environment has been interrupted and persistency, that is to say, repeated reinfestation of the animal with parasites endemic to the environment is eliminated.

Advantageously, the magazine strip 16 may be loaded for selective injection of any number of immediate release pellets 14 or extended release pellets 16 in order to obtain delivery of a selected dosage by each formulation tailored to the species, weight, age or sex in a wide variety of animals. Where a number of pellets of each formulation of pellets 14 and 16 are to be delivered, the pellets may be alternated. In other embodiments, both immediate and delayed release antiparasitic pellets 14 and 16 may be alternated in a stack of pellets of other pharmaceuticals, for delivery through the implant receiving puncture 28.

The pellet system 10 of the present invention may be employed efficaciously with cows, sheep, swine, goats, poultry, horses, dogs, cats or any other suitable animal, including wild animals and humans.

The following example is provided for the purpose of illustrating the invention and is not intended to be limiting upon the scope of the claims.

EXAMPLE 1

A quick release pellet is produced including 100 milligrams of ivermectin in a quick release matrix of lactose and microcrystalline cellulose as a disintegration aid. A set of five sustained released pellets is formulated and formed containing a total of 125 milligrams of ivermectin in a controlled and sustained release matrix of polyethylene glycol. Thereafter, all six pellets are implanted under the skin in the ear of a cow.

It is to be understood that while certain forms of the present invention have been illustrated and described herein, it is not to be limited to the specific forms or arrangement of parts described and shown.

What is claimed and desired to be secured by Letters Patent is as follows:

1. A method for providing immediate and long term control of parasite infestation in an animal; said method comprising:
    (a) providing an implanter apparatus for implanting parasiticidal pellets in an animal's ear through a bore of a hypodermic needle which is operably coupled to a pellet magazine;
    (b) loading the pellet magazine with at least one immediate release parasiticidal agent pellet dose and at least one extended release parasiticidal agent pellet dose wherein each parasiticidal agent pellet dose separately comprises from about 25–175 mg of at least one parasiticidal agent and wherein said immediate release pellet dose is configured to release substantially all of said parasiticidal agent present therein into said animal;
    (c) inserting the hypodermic needle under the skin of an animal's ear and injecting said at least one immediate release pellet dose and said at least one extended release pellet dose; and
    (d) withdrawing the hypodermic needle from under the skin of the animal's ear thereby leaving said at least one immediate release pellet dose and said at least one extended release pellet dose beneath the skin of the animal's ear.

2. The method according to claim 1 wherein said immediate release and said extended release parasiticidal agent pellet doses separately comprise a parasiticidal agent selected from the group consisting of avermectins, milbemycins, milbemycin oximes, fenbendazoles, lufenerons, derivatives and mixtures thereof.

3. The method according to claim 2 wherein said parasiticidal agent comprises an avermectin selected from the group consisting of ivermectin, doramectin, moxidectin, eprinomectrin, abamectin, derivatives and mixtures thereof.

4. The method according to claim 1 further comprising the step of providing a plurality of discrete pellet doses.

5. The method according to claim 4 further comprising the step of providing at least one discrete immediate release dose in a first pellet and at least one discrete extended release dose in a second pellet.

6. The method according to claim 1 further comprising the steps of:
    (a) inserting the hypodermic needle under the skin of an animal's ear and injecting said at least one immediate release pellet dose;
    (b) maintaining the hypodermic needle in place under the skin of the animal; and
    (c) sequentially injecting said at least one extended release pellet dose.

7. In a method of administering a subcutaneous implant to an animal, the improvement comprising the step of injecting an implant for retention under the skin of an animal's ear, said implant comprising an immediate release parasiticidal agent dose and an extended release parasiticidal agent dose in a single injection wherein each parasiticidal agent pellet separately comprises from about 25–175 mg of at least one parasiticidal agent and wherein said immediate release pellet dose is configured to release substantially all of said parasiticidal agent present therein into said animal.

8. A method for providing immediate and sustained parasiticide release in an animal comprising the steps of;
    (a) providing an implanter apparatus for implanting pharmaceutical pellets in an animal through a bore of a hypodermic needle which is operably coupled to a pellet magazine;
    (b) loading the pellet magazine with an immediate release parasiticidal agent pellet dose and an extended release parasiticidal agent pellet dose wherein each parasiticidal agent pellet dose separately comprises from about 25–175 mg of at least one parasiticidal agent and wherein said immediate release pellet dose is configured to release substantially all of said parasiticidal agent present therein into said animal;
    (c) inserting the hypodermic needle under the skin of the animal's ear and selectively injecting the immediate release pellet dose;
    (d) simultaneously with the step of paragraph (c) also injecting the extended release parasiticidal agent pellet dose; and
    (e) withdrawing the hypodermic needle from under the skin of the animal while leaving both of said immediate release and extended release doses beneath the skin of the animal's ear.

* * * * *